United States Patent [19]

Schreiber, Jr.

[11] 4,375,882
[45] Mar. 8, 1983

[54] IN-LINE FLOW CONTROL APPARATUS

[76] Inventor: Lloyd J. Schreiber, Jr., 211 Cloverdale Dr. Rte. 1, Whitley Heights, Clayton, N.C. 27520

[21] Appl. No.: 200,987

[22] Filed: Oct. 27, 1980

[51] Int. Cl.³ .............................................. F16K 7/12
[52] U.S. Cl. ................... 251/266; 251/331; 251/368; 128/274; 128/214 R
[58] Field of Search ................ 251/331, 266, 368

[56] References Cited

U.S. PATENT DOCUMENTS 3,151,838  10/1964  Tripoli et al. ............... 251/331 X
4,072,292   2/1978  Banon ........................ 251/331
4,280,680   7/1981  Payne ........................ 251/331 X

FOREIGN PATENT DOCUMENTS 261979    5/1963  Australia ..................... 251/331
1775475   7/1971  Fed. Rep. of Germany ......... 251/331

Primary Examiner—Arnold Rosenthal
Attorney, Agent, or Firm—H. Gordon Shields

[57] ABSTRACT

In-line flow control apparatus for intravenous solutions includes a housing inserted in a conduit carrying liquids and includes a housing connected to the conduits with a valve disposed within the housing and a valve core disposed within the valve movable in response to rotation of a screw for controlling the flow of the liquid through the apparatus from one portion of the conduit to the adjacent portion of the conduit.

4 Claims, 6 Drawing Figures

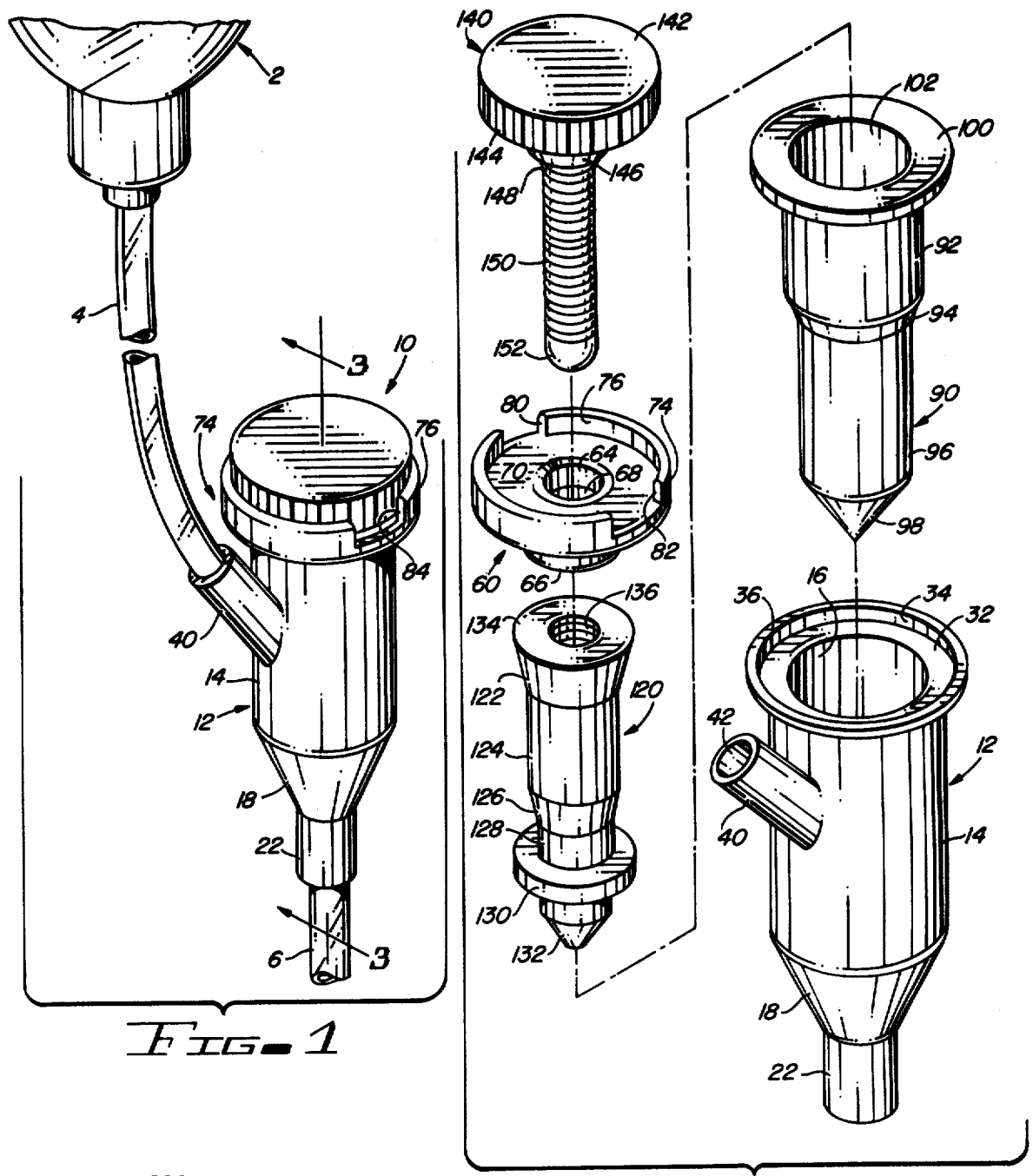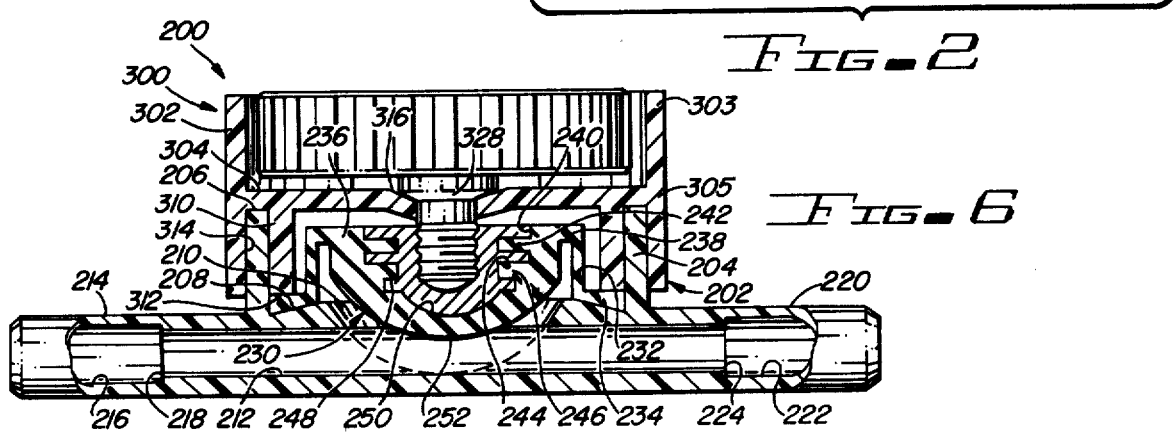

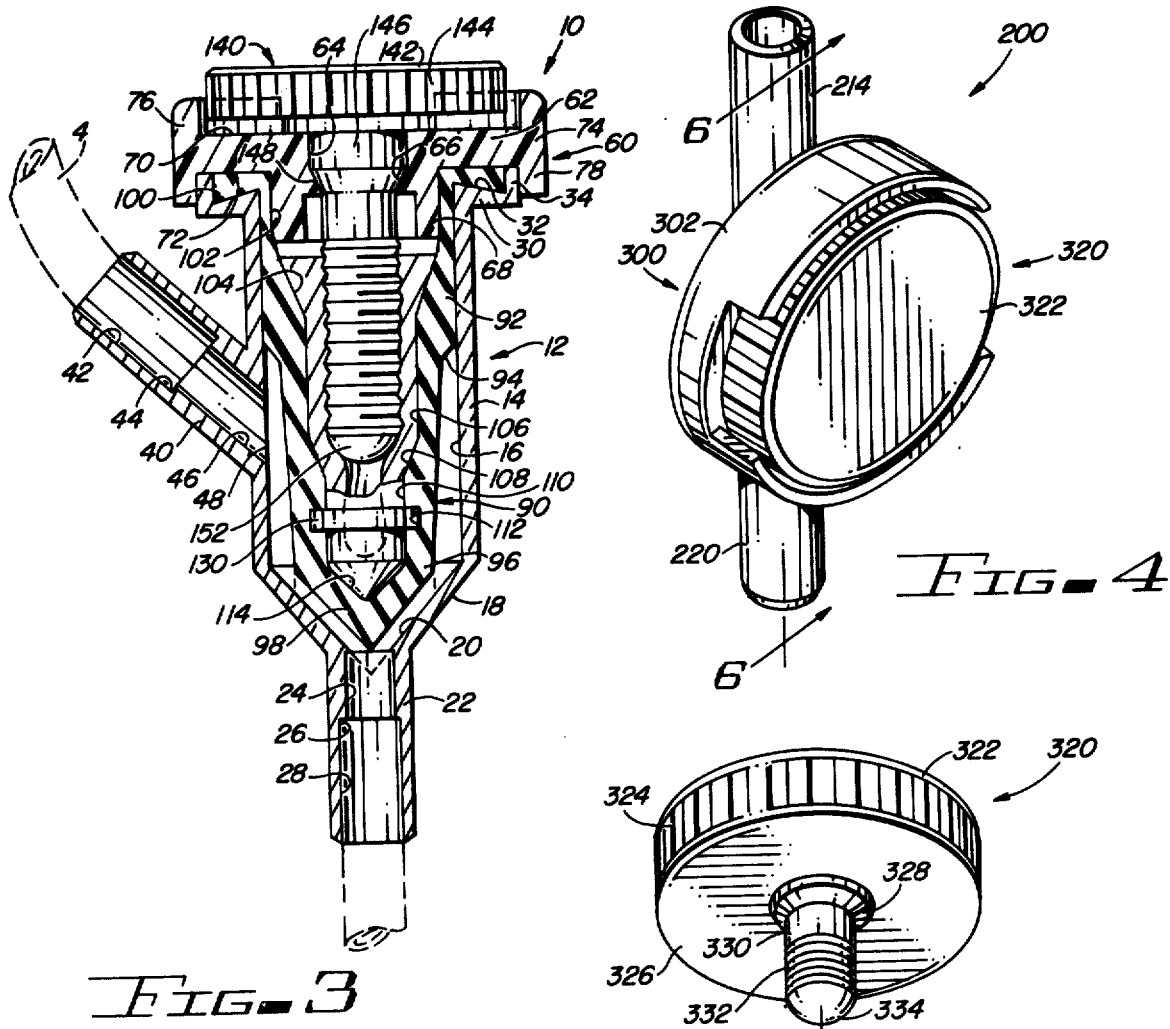
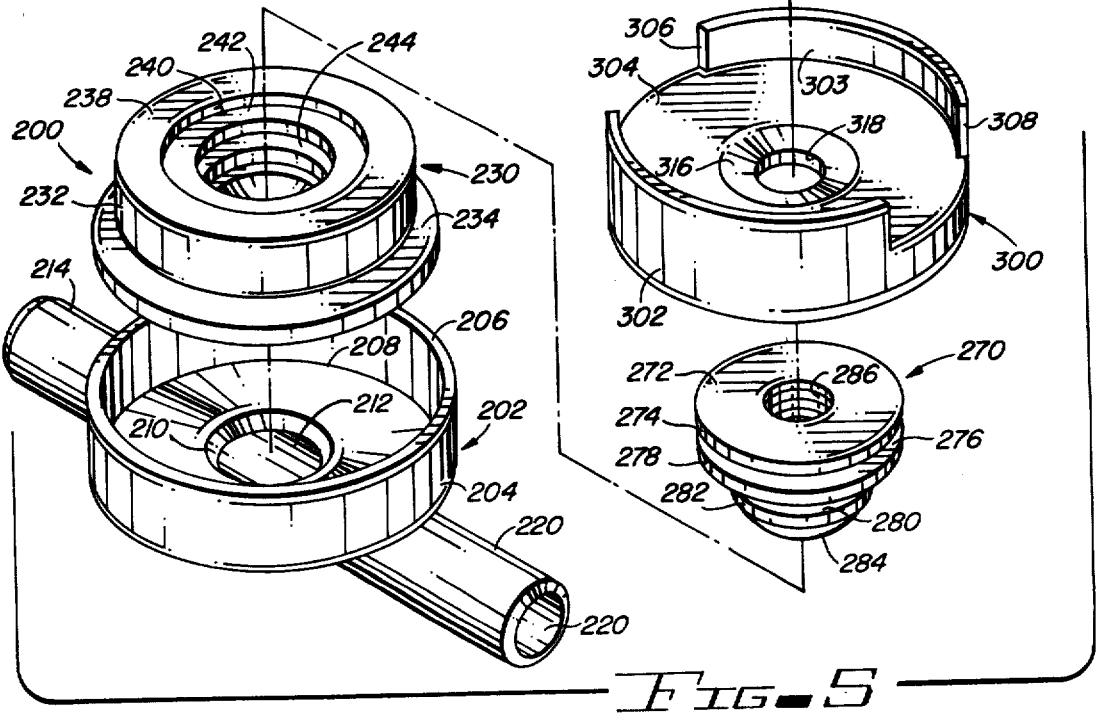

IN-LINE FLOW CONTROL APPARATUS

BACKGROUND OF THE INVENTION

1. Field of the Invention

This invention relates to flow control apparatus and, more particularly, to in-line flow control valves for controlling the flow of a liquid through a conduit.

2. Description of the Prior Art

As is well known and understood, the valve art for controlling the flow of liquids is a relatively old art. However, the application of the valve art to the flow of intravenous solutions is somewhat limited. In the medical arts there are two primary types of mechanical flow control devices. One type is the screw clamp, and the other type is the roller clamp. The screw clamp includes a screw and a screw housing. The housing is situated so that as the screw is turned, the tip of the screw presses against the flat surface. Medical tubing, which is flexible, is disposed on one side of the flat surface against which the tip of the screw bears. Essentially, the tubing extends between a pair of flat surfaces, one of which is fixed and the other of which is movable by the screw. As the screw is tightened against the movable flat element, the flow through the tubing is restricted.

There are several problems associated with this type of clamp. For example, the clamp usually requires two-handed operation, one hand for holding the clamp and the other hand for adjusting the screw. Moreover, the clamp may slide up and down on the tubing, often within reach of the patient. As the patient moves, the motion of the tubing may cause the flow through the clamp to wander. Another problem is the lack of consistency of the medical tubing, both in terms of stiffness of the tubing and in the wall thickness of the tubing, which reflects the flow rate through the tubing.

The second type of clamp, the roller clamp, includes a roller in a track that is disposed adjacent to or above a flat incline. The medical tubing is run between the roller and the incline. As the roller is moved, it presses on the tubing and restricts the flow of fluid. The roller is spring biased against the tubing and the incline.

The roller type clamp can, like the screw clamp, move up and down on the tubing, often staying within the reach of the patient. As the patient moves, the motion of the tubing itself may cause a change in the position of the roller, which may result in a change in the flow rate to the tubing. The varying stiffness, or softness, of the tubing may cause the clamp to function in a normal manner, as designed, at times, and at other times may result in a flattening of the tubing, either restricting the flow substantially or even stopping the flow.

If the wall thickness varies, the incline may either not restrict the flow of fluid at all, or it may stop the flow. In order to compensate for this type of problem, the incline must extend over a relatively long distance, or else the rate of incline must substantially increase. Either alternative makes the clamp relatively bulky or eliminates some of the adjustment capability that a flow control device must have.

The in-line flow control valve apparatus of the present invention overcomes the problem of the prior art, as discussed above, by being insertable in the line or tubing. The flow of fluid or liquid is accordingly through the valve rather than through a restricted portion of the tubing or line itself.

While in-line flow control devices have not heretofore been developed for use in the medical field, flow control devices, using diaphragms, are relatively old and relatively well-known. Some examples of in-line diaphragm type valves are shown in the patents discussed below.

U.S. Pat. No. 1,800,157 discloses a diaphragm type valve with the diaphragm not directly connected to the actuator. Fluid pressure actuates the diaphragm to allow fluid to flow through the valve. The actuator is secured to a threaded rod and accordingly moves vertically as the threaded rod is rotated. The flow through the valve depends on two variables; one, the flow or the pressure of the fluid, and two, the position of the actuator.

U.S. Pat. No. 2,191,863 discloses a diaphragm valve with the diaphragm secured to the actuator. A threaded rod is secured to the actuator, and rotation of the rod accordingly results in vertical movement of the actuator. There is a relatively loose fit between the actuator and the threaded rod which allows relative movement therebetween, and accordingly a variation in the flow through the valve. Obviously, the precise control of the fluid flow through the valve is not of substantial importance with respect to the 2,191,863 patent.

U.S. Pat. No. 2,705,124 discloses a screw secured to a diaphragm and to a diaphragm actuator. Relative movement between the diaphragm and the diaphragm actuator is provided by a loose fit between the diaphragm actuator and a nut secured to the rod and held in place by the actuator. A threaded rod extends through the nut and into the diaphragm. As with the above patents, the precision control of fluid through the valve is ot of paramount importance.

U.S. Pat. No. 2,939,676 discloses another type of diaphragm valve in which a screw extends through a nut held in place by the valve housing. The screw is not secured to the diaphragm, but rather the nut, which moves vertically as the screw is turned, abuts a block secured to the diaphragm to limit the vertically upwardly movement of the block and accordingly of the diaphragm. Fluid pressure in the line causes the valve diaphragm to move until the nut is disposed directly against the block. The screw may be rotated to prevent flow through the valve, but if the screw is rotated to raise the nut, then the pressure of the liquid flowing through the line forces the diaphragm and the block away from the valve seat to allow the fluid to flow. As in the 1,800,157 patent, discussed above, the flow to the valve is a function of the pressure of the fluid flow in the line and the location of the nut secured to the threaded rod.

U.S. Pat. No. 2,953,346 is similar to the apparatus of the 2,191,863 patent, discussed above. A loose fitting nut is prevented from rotating and accordingly moves axially or vertically with respect to a screw which extends through the nut. The nut is secured by a relatively loose connection through the diaphragm actuator to provide vertical movement of the diaphragm for opening and closing the fluid passage through the valves. As with the other patents discussed above, the accuracy or precise control of the flow of liquid through the valve is not of primary concern with the apparatus of the 2,953,346 patent.

U.S. Pat. No. 3,275,291 discloses a diaphragm secured to a threaded sleeve which is in turn secured to a threaded rod. Rotation of the threaded rod causes the sleeve and the diaphragm to move vertically upwardly and downwardly. A relatively thin membrane is associated with the diaphragm, and the membrane and diaphragm together control the flow through a fluid passage in the valve. The membrane is not movable in response to the rotation of the threaded rod. Rather, when the diaphragm is moved away from the membrane, the pressure of the fluid causes the membrane to move away from its valve seat to allow the fluid to flow through the valve. The membrane includes an opening or aperture on its downstream side. When the downstream pressure exceeds the upstream pressure, fluid flows into a chamber between the membrane and the diaphragm and the pressure then causes the membrane to move to the valve seat to cut off the flow of fluid. The valve accordingly closes due to a pressure differential between the upstream and the downstream pressures when the upstream pressure is less than the downstream pressure. The diaphragm or the valve may also be closed when the diaphragm is moved vertically downwardly by rotation of the threaded rod. The downward rotation of the threaded rod causes the diaphragm to move downwardly against the membrane. As with the above patents, the precise control of the flow of liquid or flow through the valve is not of primary concern.

U.S. Pat. No. 3,666,230 discloses a valve in which a screw turns in a threaded portion of a valve body and allows fluid pressure to move a diaphragm against the screw. A second embodiment of the 3,666,230 apparatus utilizes a piston rather than a rotating screw to move a valve actuator either towards or away from the diaphragm. Fluid pressure on the piston allows the piston to move away from the valve actuator or toward the valve actuator, and the pressure of the fluid in the line through the valve results in the opening of the valve. As with the above patents, accuracy of flow through the valves is not of primary concern.

It will be noted that none of the above discussed patents are concerned with accuracy of flow of the fluid through a valve. Moreover, none of the patents is concerned with fluid flow for medical purposes. The apparatus of the present invention is primarily concerned with the precise control of fluid or liquid for medical purposes, using a diaphragm type valve to control fluid flow from one line to another with the assurance of maintaining a sterile fluid path.

SUMMARY OF THE INVENTION

The apparatus of the present invention comprises an in-line valve for controlling fluid flow by the precise positioning of a diaphragm in the fluid path actuable by one handed operation.

Among the objects of the present invention are the following:

To provide new and useful valve apparatus;

To provide new and useful in-line valve apparatus for contolling the flow of fluids;

To provide new and useful apparatus for controlling the flow of intravenous fluids;

To provide new and useful valve apparatus having a movable diaphragm;

To provide new and useful apparatus for controlling the flow of fluid by positioning a diaphragm;

To provide new and useful valve apparatus having a valve core secured to and movable with a flexible diaphragm; and To provide new and useful valve apparatus having a valve core secured to and movable with a flexible diaphragm to insure the integrity of a sterile fluid path.

BRIEF DESCRIPTION OF THE DRAWING

FIG. 1 is a perspective view of the apparatus of the present invention in its use environment.

FIG. 2 is an exploded perspective view of the valve apparatus of the present invention.

FIG. 3 is a view in partial section of the apparatus of FIG. 1, taken generally along line 3—3 of FIG. 1.

FIG. 4 is a perspective view of an alternate embodiment of the apparatus of the present invention.

FIG. 5 is an exploded perspective view of the apparatus of FIG. 4.

FIG. 6 is a view in partial section of the apparatus of FIG. 4, taken generally along line 6—6 of FIG. 4.

DESCRIPTION OF THE PREFERRED EMBODIMENT

FIG. 1 is a perspective view of flow control apparatus 10 of the present invention connected to an intravenous (I.V.) solution bottle 2 by clear plastic medical tubing 4. FIG. 2 is an exploded perspective view of the flow control apparatus 10 of FIG. 1, with the component elements of the apparatus 10 spaced apart from each other. FIG. 3 is a view in partial section of the flow control apparatus 10 of FIG. 3, taken generally along line 3—3 of FIG. 1. For the following discussion of the flow control apparatus 10, reference will be made to FIGS. 1, 2, and 3.

Flow control apparatus 10 is designed to be connected to an I.V. bottle 2 by clear, generally plastic, flexible tubing 4. The flow control apparatus 10 includes a housing 12 into which the I.V. solutions flow from the bottle 2 through the tubing 4. The housing 12 includes a generally cylindrical portion 14 and a conical portion 18 disposed below and comprising a continuation of the cylindrical portion 14. Within the cylinder 14 is a bore 16. Within the conical portion 18 is a conical bore 20 which defines a seat for a valve 90. The movement of the valve 90 with respect to the conically tapered bore or seat 20 controls the flow of the I.V. fluid through the apparatus 10.

Beneath the conical portion 18 is a lower stem 22. The lower stem 22 includes an interior bore 24 which comprises an outlet bore through which the I.V. fluid flows. Within the bore 24 is a shoulder 26 which extends radially outwardly with respect to the bore 24. The shoulder 26 comprises a transition area between the bore 24 and the bore 28. As shown in phantom (dotted line) in FIG. 3, outlet tubing 6 extends into the bore 28 and is disposed against the shoulder 26. I.V. fluid accordingly flows from the bore 24 directly into the tubing 6. Viscosity is generally not a factor in controlling the flow of I.V. fluids or liquids.

The upper portion of the housing 12 includes an outwardly extending flange 30. Extending upwardly from the outer portion of the flange 30 is a vertical wall 34. The wall 34 is generally parallel to the cylinder 14. A downwardly and outwardly tapering seat 32 is defined on the top or upper portion of the flange 30 between the bore 16 and the wall 34. The wall 34 terminates upwardly in a rim 36.

I.V. fluid flows into the bore 16 of the cylindrical portion 14 of the housing 12 through an inlet stem 40. The inlet stem 40 is disposed at an acute angle with respect to the longitudinal axis of the cylinder 14. Within the stem 40 are two bores, an upper, connecting bore 42 and a lower, inlet bore 46. A shoulder 44 extends radially between the two bores 42 and 46. The upper, connecting bore 42 has a diameter slightly greater than that of the lower, inlet bore 46. The shoulder 44 accordingly provides a transition between the two bores. As best shown in FIG. 1, I.V. tubing 14 extends into the bore 42 and is disposed against the shoulder 44. I.V. fluid accordingly flows through the tubing 4, into the bore 46, and through an opening 48 in the cylinder wall 14 into the bore 46, and through an opening 48 in the cylinder wall 14 into the bore 16. The opening 48 provides direct communication between the bore 46 and the cylinder bore 16.

The flow of the I.V. fluid from the bore 16, downwardly through the conical bore or valve seat 20 and into the lower stem 22, is controlled by a valve shell 90. The valve shell 90 is flexible and accordingly acts as a diaphragm to control the flow of the I.V. fluid between the bore 16 and the outlet bore 24 through the conical bore 20.

The valve shell 90, best shown in FIG. 2, includes an upper cylindrical portion 92 and a lower cylindrical portion 96. The respective diameters of the upper and lower cylindrical portions are different, with the diameter of the upper cylindrical portion 92 being greater than the diameter of the lower cylindrical portion 96. A tapered shoulder 94 extends between the lower part of the upper cylindrical portion 92 and the upper part of the lower cylindrical portion 96.

The valve shell 90 terminates in a conical tip 98. The conical tip 98 is disposed within the conical portion 18 of the housing 12, as best shown in FIG. 3. Movement of the conical tip portion 98 of the valve shell 90 with respect to the conical bore 20 of the housing determines the rate of flow of the I.V. fluid through the flow control apparatus 10. In FIG. 3, there is shown in phantom the conical tip 98 disposed at the lower portion of the conical bore 20, thus stopping the flow of I.V. fluid through the apparatus 10 when the valve shell is fully seated in the conical bore and on the valve seat 20.

At the upper portion of the valve shell 90 there is a flange 100 which extends outwardly from the top of the upper cylinder portion 92. The flange 90 includes a downwardly and outwardly tapering lower portion which is disposed on the tapered seat 32 of the housing 12. The outer portion of the flange 100 defines a rim which is disposed against the inner periphery of the vertical wall 34 of the housing 12.

The valve shell 90 includes several bores, as best shown in FIG. 3. Extending downwardly within the upper cylindrical portion 92 is an upper cylindrical bore 102. The length of the upper cylindrical bore 102 is relatively short. Extending downwardly and inwardly from the lower portion of the upper cylindrical bore 102 is an upper tapered bore 104. Extending downwardly from the lower portion of the upper tapered bore 104 is a central cylindrical bore 106. The length of the central cylindrical bore 106 is greater than the length of the upper cylindrical bore 102. Extending downwardly and inwardly from the lower portion of the central cylindrical bore 106 is a central tapered bore 108. The length or height of the central tapered bore 108 is relatively short, as compared with the central cylindrical bore 106. Finally, a lower tapered bore 114 extends downwardly and inwardly from the lower cylindrical bore 110. The bore 114 is disposed at the bottom of the valve shell 90 and within the conical tip 98. A groove 112 extends radially outwardly from the lower cylindrical bore 110 and into the lower cylindrical portion 96 of the valve shell 90. The groove 112 is disposed about midway between the central tapered bore 108 and the lower tapered bore 114. The groove or slot 112 is annular.

For securing the valve shell 90 in place with respect to the housing 12, a cap 60 is used. The cap 60 includes a top plate 62 which is of a generally flat, circular configuration. The plate 62 includes a central aperture 64. The aperture 64 is a relatively short cylindrical bore, the lower end of which is connected to an inwardly tapering conical bore 66.

Extending downwardly from the plate 62 of the cap 60, and adjacent the tapered bore 66, is a cylinder wall 68. The cylinder wall 68 is of a slightly greater diameter than the bore 64. The wall 68 extends downwardly, below both bores 64 and 66. The outer diameter of the cylinder wall 68 is about the same as the inner diameter of the upper bore 102 of the valve shell 90.

The plate 62 includes a generally flat, planar upper surface 70, and a generally flat, planar bottom surface 72. The surfaces 70 and 72 are substantially parallel to each other. The bottom surface 72 extends between the cylindrical portion 68 and an outer flange 74. The flange 74 extends above the upper surface 70 of the plate 62 and below the lower or bottom surface 72 of the plate 62. The flange 74 may be divided into two portions, an upper portion 76 and a lower portion 78. The upper portion 76 extends above the top surface 70, and the bottom portion 78 extends below the lower surface 72.

As best shown in FIG. 2, there are two slots 80 and 82 extending through the upper portion 76 of the flange 74. The purpose of the slots 80 and 82 will be discussed below in conjunction with a screw 140 which is used to move the valve 90 vertically upwardly and downwardly to control the flow of I.V. fluid to the apparatus 10.

The valve shell 90 is secured to the housing 12 by means of the cap 60. The flange 100 of the valve shell 90, as shown in FIG. 3, is disposed on the tapered seat 32 of the flange 30 of the housing 12. With the remainder of the valve shell 90 disposed within the housing 12, the cap 60 is then secured to the housing 12.

The bottom surface 72 of the plate 62 is disposed on the top or rim 36 of the wall 34, and the downwardly extending cylindrical wall 68 of the cap 60 is spaced apart from the cylinder 14 of the housing 12, with the upper cylindrical portion 92 of the valve 90 disposed between the cylinder wall 14 of the housing 12 and the cylinder wall 68 of the cap 60. The top or upper portion of the flange 100 is disposed against the lower surface 72 of the plate 62. With the cap 60 then welded to the housing 12, the valve 90 is fastened securely to the housing and the cap to define a single, integral unit. The valve or valve shell 90 is, of course, flexible, and acts as a diaphragm when appropriately moved within the housing 12 to control the flow of I.V. fluid through the flow control apparatus 10. When the cap 60 is secured, as by solvent welding, to the housing 12, the two portions become a single structural entity, not movable relative to each other. Movement of the diaphragm or valve 90 is the accomplished by the cooperative movement of a valve core 120 and a screw 140.

The valve core 120 is configured, with respect to its outer periphery, to fit within the valve 90. The valve core 120 includes an upper tapered portion 122 which mates with the upper tapered bore 104 of the valve 90. The valve core 120 also includes an upper cylindrical portion 124, which is disposed below or beneath the upper tapered portion 122. The upper cylindrical portion 124 mates with, or is disposed within, the central cylindrical bore 106 of the valve 90. Below the cylindrical portion 122 is a central tapered portion 126, which corresponds to, and mates with, the central tapered bore 108 of the valve 90. Beneath the central tapered portion 126 is a lower cylindrical portion 128, which corresponds to, and mates with, the lower cylindrical bore 110 of the valve 90. Extending outwardly from the lower cylindrical portion 128 of the valve core 120 is a round locking flange 130. The flange 130 extends into the annular groove 112 of the valve 90 to secure the valve core 120 and the valve 90 together.

The valve core 120 terminates below the lower cylindrical portion 128 in a somewhat rounded, conical lower tip 132. As shown in FIG. 3, the tip 132 extends into the tapered bore 113 of the valve 90.

The valve core 120 comprises an insert that fits within the valve or valve shell 90. The valve shell 90 and the valve core 120 together comprises a movable valve which is disposed within the bore 16 of the cylinder 14.

The valve core 120 is not flexible as is the valve shell or diaphragm 90. Rather, it is relatively inflexible or rigid. However, it is disposed within the valve shell or diaphragm, with the two elements secured together by means of the flange 130 extending into the groove 112 to secure the two elements together for joint movement.

Movement of the valve shell 90 and the valve core 120 is accomplished by rotation of the screw 140 which is threadedly secured to the valve core 120. The valve 120 includes a threaded interior bore 136. The bore 136 extends downwardly, coaxially with respect to the various portions, both cylindrical and conically tapered, of the valve core 120. The bore 136 is internally threaded to receive, and matingly engage with a threaded shank 150 of the screw 140.

The stem 146 includes a tapered flange portion 148 which defines a bearing surface and a transition surface between the stem 146 and a threaded shank 150. As perhaps best shown in FIG. 3, the head 142 of the screw 140 is disposed on top of the cap 60, with the threaded shank and the stem extending downwardly through the aperture or bore 64 and through the conically tapered bore or seat 66 of the cap 60. The diameter of the stem 146 is slightly less than that of the bore 64. The tapered flange or boss 148 is disposed against the conical tapered bore or seat 66 of the cap 60.

The head 142 is disposed within the upper portion 76 of the flange 74, and above the top surface 70 of the cap 60. The upper flange portion 76 defines a relatively short cylindrical portion into which the head 142 extends. As best shown in FIG. 1, the slots 80 and 82 allow the tips of the user's thumb and finger to bear against the knurled outer periphery 144 of the screw 140 to rotate the screw in a clockwise or counterclockwise direction, as desired, to move the valve and valve core within the housing 12 and with respect to the tapered bore or valve seat 20 to control the flow of fluid therethrough.

The threaded shank 150 matingly engages the threads on the interior bore 136 of the valve core. The bottom of the screw 140 includes a rounded bottom tip 152, below the threaded shank 150. The tip 152 is disposed within a mating portion, appropriately configured, on the interior of the valve core 120. This is best shown in FIG. 3.

As best shown in FIG. 3, the movement of the diaphragm or valve shell 90 and the valve core 120 is limited vertically upwardly and downwardly. The vertically upwardly movement of the valve core 120 is limited by the vertical space or distance between the top or upper portion 134 of the valve core 120 and the bottom of the cylinder wall 68 of the cap 60. The downward movement of the valve 90 and valve core 120 is limited by the conical bore or valve seat 20. However, between the physical constraints of the structure, as discussed, the valve core 120, and the valve shell 90, secured thereto, moves vertically upwardly and downwardly in response to rotation of the screw 140 by a user. A rotation of the screw 140 results in a vertical movement of the valve shell 90 with respect to the valve seat 20 to control the flow of fluid from the bore 46 of the inlet stem 40, through the bore 16 between the valve shell 90 and the cylinder 14, and through the outlet bore 24 in the lower stem 22. As a practical matter, the vertical movement of the valve shell and its core need only be a few thousandths of an inch to appropriately control the flow of an I.V. fluid or liquid.

The vertical movement of the valve per revolution of the screw 140 is, of course, dependent upon the pitch of the threads of the threaded shank 150 and the threaded bore 136, and the relative diameters of the threaded shank 150 and the head 142. The larger the head 142 with respect to its diameter vis-a-vis the diameter of the shank 150, and the finer the pitch of the threads, the more precise may be the control of the fluid through the flow control apparatus 10 because of the very small or minute required vertical movements of the valve with respect to the valve seat 20.

An alternate embodiment of the flow control apparatus 10 of FIGS. 1-3 is shown in FIGS. 4-6. An in-line flow control apparatus 200 is illustrated in FIGS. 4-6. FIG. 4 comprises a perspective view of the in-line flow control apparatus 200, and FIG. 5 comprises a perspective, exploded view of the flow control apparatus 200. FIG. 6 is a view in partial section of the flow control apparatus 200 of FIG. 4, taken generally along line 6—6 of FIG. 4. For the following discussion, reference will be made to FIGS. 4, 5, and 6.

The in-line flow control apparatus 200 has elements which generally correspond to the elements of the flow control apparatus 10 of FIGS. 1-3, including a housing 202, a valve shell 230, a valve core 270, a cap 300, and a screw 320. The housing, valve shell, valve core, cap, and screw, of the in-line flow control apparatus 200, perform functions essentially similar to the functions performed by their counterpart elements in the flow control apparatus 10. However, the structure of the various elements of the in-line flow control apparatus 200 is different from the general structure of the flow control apparatus 10.

The housing 202 of the flow control apparatus 200 includes a cylindrical portion 204 connected to a pair of hollow stems 214 and 220. The stem 214 may be referred to as an inlet stem, and it accordingly includes an inlet bore 216. The stem 220 may be considered as an outlet stem and it accordingly includes an outlet bore 222. The bores 216 and 222 communicate with a fluid bore 212 which extends through the housing 202 at the bottom part thereof, below the cylindrical portion 204.

The cylinder 204 includes a top 206 which cooperates with the cap 300, as will be discussed below, for purposes of securing the valve shell 230 to the flow control apparatus 200.

The lower portion of the cylinder 204, remote from its top 206, includes a tapered floor 208, which is best shown in FIG. 5. The tapered floor 208 defines a bottom end wall for the cylinder 204. The floor 208 tapers upwardly and inwardly from the bottom of the cylinder 204. The floor 208 is generally circular in configuration. A tapered valve seat or aperture 210 extends through the floor 208. The seat 210 tapers inwardly and downwardly from the center of the floor 208, and is accordingly coaxially aligned with the cylinder 204 of the housing 202. The inward and downward taper of the seat 210 extends to the bore 212 to allow communication between the interior of the cylinder 204 and the bore 212.

As best shown in FIG. 6, the diameter of the fluid bore 212 is slightly less than the diameters of the inlet and outlet bores 216 and 222, respectively. Between the fluid bore 212 and the inlet and outlet bores 216 and 222 is a pair of shoulders 218 and 224, respectively. The shoulders 218 and 224 comprise a transition area or portion between the fluid bore 212 and the respective inlet and outlet bores 216 and 222. As best illustrated in FIG. 1, and as shown in phantom in FIG. 3 for the valve apparatus 10, and which is comparable to, and thus also illustrative of, the valve apparatus 200, fluid carrying tubing or conduits extend into the bores 216 and 222 and abut against the shoulders 218 and 224, respectively, to allow fluid to flow through the flow control apparatus 200.

The valve shell 230 is flexible, like the valve shell 90 of the flow control apparatus 10. The valve shell 230 accordingly acts as a diaphragm in its vertical movement (see FIG. 6) with respect to the housing 202 and the fluid bore 212.

In general configuration, the valve shell 230 includes an outer cylindrical portion 232 and an inner cylindrical portion 236 connected by a connecting web 238. The outer cylindrical portion 232 includes a radially outwardly extending flange 234 which, when the valve shell 230 is disposed within the housing 202, rests on the floor 208. The flange 234 extends outwardly from the bottom portion of the outer cylinder 232. The connecting web 238 extends radially inwardly from the top or upper portion of the outer cylinder 232 to connect with the top or upper portion of the inner cylinder 236.

The inner cylinder 236 includes an upper bore 240 which extends downwardly a relatively short distance. Extending radially inwardly from the lower portion of the upper bore is an upper flange 242. A lower flange 246 extends radially inwardly generally parallel to, and spaced a relatively short distance downwardly from, the upper flange 242. Between the upper flange 242 and the lower flange 246 is a slot or groove 244. Beneath the lower flange 246 is a lower slot 248. The slots 244 and 248, and the upper bore 240, receive portions of the valve core 270, as will be discussed below. The upper bore 240 is, for all practical purposes, simply a shoulder above the upper flange 242 at the juncture of the inner cylinder 236 and the connecting web 238.

The inner cylinder 236 is closed at its bottom portion by a concavity 250. The exterior of the concavity 250 defines a convex bottom or tip 252. The convex bottom 252 is disposed within the aperture defined by the tapered valve seat 210 of the housing 202. The convex bottom 252 extends through the tapered valve seat 210 and moves vertically upwardly and downwardly from the position shown in FIG. 3 with respect to the bore 212 and the valve seat or aperture 210 in the floor 208 of the cylinder 204 to control the flow of fluid through the bore 212. When the convex bottom 252 is in the down position shown in dotted line in FIG. 6, the fluid flow in bore 212 will be stopped. A portion of the convex bottom 252 will be against the valve seat 210 and a portion of the convex bottom will extend through the valve seat to the dotted line position, closing off the fluid flow in the bore 212.

The valve core 270 is relatively rigid. It cooperates with the diaphragm or valve shell 230 and the screw 320 to control the flow of fluid through the fluid bore 212.

The valve core 270 includes a generally flat, or planar, top portion 272 with a central threaded bore 286 extending downwardly through the valve core 270.

The valve core 270 is of a generally cylindrical configuration, with three flanges extending radially outwardly therefrom. The radially outwardly extending flanges are spaced apart vertically from each other. A top or upper flange 274 is a continuation of the top or outer planar surface 272 remote from the central bore 286.

Disposed below the upper flange 274, and spaced apart therefrom, is a middle flange 278. An upper slot 276 is disposed between the upper flange 274 and the middle flange 278.

Spaced apart downwardly from the middle flange 278 is a lower flange 282. A lower slot 280 is defined between the middle flange 278 and the lower flange 282. A convex bottom 284 extends downwardly from the lower flange 282.

The upper flange 274 cooperates with, and is disposed on, the upper bore or shoulder 240 of the valve shell 230. The middle flange 278 extends into the slot 244 of the valve shell 230, and the lower flange 282 extends into the lower slot 248 of the valve shell 230. The upper flange 242 of the valve shell 230 extends into the upper slot 276 of the valve shell 270, and the lower flange 246 of the valve shell 230 extends into the lower slot 280 of the valve core 270. A mating or interleaving engagement is thus provided to secure the valve shell and the valve core together.

The convex bottom 284 of the valve core 270 extends into, and matingly engages with, the concave bottom 250 of the inner cylinder 236 of the valve shell 230.

Extending downwardly from the top surface 72, centrally with respect to the valve core 270, is an internally threaded or tapered bore 286. The bore 286 cooperates with the screw 320 to move the valve shell 230 and the valve core 270 relative to the housing 202 and the bore 212. The valve shell 230 and the valve core 270, held together by the interleaved flanges and slots or grooves, move together as the screw 320 is rotated.

For securing the valve shell 230, and its valve core 270, to the housing 202, the cap 300 is used. The cap 300 includes a cylindrical wall 302 with a central wall 304 dividing the cylinder wall 302 into an upper portion 303 and a lower portion 305. The upper portion 303 of the cylinder wall 302 includes a pair of slots 306 and 308 which are disposed diametrically opposite each other and extend upwardly from the central wall 304.

The central wall 304 includes an inner bore or aperture 318 which extends through the wall 304. A conically tapered portion 316 extends from the bore 318 upwardly and outwardly to the wall 304. The conically tapered portion 316 is disposed about the bore or aperture 318.

Spaced inwardly from the lower portion 305 of the cylinder wall 302, and substantially parallel thereto, and extending downwardly from the bottom of the central wall 304, is an inner cylinder or cylinder wall 310, best shown in FIG. 6. The bottom of the cylinder wall 310 is identified in FIG. 6 by reference numeral 312. As shown in FIG. 6, the walls 305 and 310 are spaced apart a relatively small or short distance from each other and they define a circular slot which receives the cylinder 204 of the housing 202.

With the radially outwardly extending flange 234 of the valve shell 230 disposed on the floor 208 of the housing 202, the cap 300 is placed on the housing. The cylinder 204 of the housing is disposed between the inner cylinder 310 of the cap and the lower portion 305 of the outer cylindrical wall 302 of the cap 300. When the cap 300 is thus in place on the housing 202, the bottom 312 of the inner cylinder 310 is disposed against the top or upper portion of the flange 234 of the valve shell 230. The valve shell 230, with its valve core 270, is accordingly secured in place within the housing 302 of the flow control apparatus 200. The cap and the housing may be appropriately secured together, as by solvent welding.

The valve shell 230 and the valve core 270, secured together, define a movable valve for controlling the flow of fluid through the bore 212 between the bores 216 and 222. Movement of the valve with respect to the bore 212 is accomplished by rotation of the screw 320.

The screw 320 includes a head 322 which is disposed outwardly from a central stem 330. The head 322 includes a knurled outer periphery 324. The knurled outer periphery aids in the positive rotation of the screw by a user by providing a friction surface for grasping between the thumb and a finger-tip of a user of the apparatus. It will be noted that the diameter of the head 322 of the screw 320 is substantially large as compared with the diameter of the stem 330.

As best shown in FIG. 5, the head 322 includes a bottom face 325. Spaced downwardly from the face 326, the stem includes an outwardly extending and conically tapered portion 328. The portion 328 comprises a bearing portion which is disposed on the tapered portion 316 of the cap 300. The lower portion of the stem 330 comprises a threaded shank 332. The bottom of the stem comprises a convexly rounded tip 334.

The internally threaded bore 286 of the valve core 270 receives the threaded shank 332 of the screw 320. Rotation of the screw 320, by rotating the head 322, results in vertically upwardly and/or downwardly movement of the valve core 270 and the valve shell 230 secured thereto. As best shown in FIG. 6, the conically tapered portion or boss 328 of the screw 320 is disposed against the tapered portion 316 of the central wall 304 of the cap 300. The two tapered portions 316 and 328 accordingly comprise bearing surfaces for the rotation of the screw 320 relative to the housing 202 and the cap 300 secured thereto.

With the screw 320 secured to the valve core 270, the head 322 is disposed within the upper portion 303 of the cylinder 302 of the cap 300, above the wall 304. The slots 306 and 308, diametrically opposite each other, allow access to the knurled outer periphery 324 of the screw 320 for rotation of the screw relative to the housing 202, cap 300, and the valve shell 230 and its core 270. Rotation of the screw 320 results in the vertically upwardly and downwardly motion of the valve, which comprises the combined valve shell and valve core, from the "up" or open position shown in FIG. 6 to the "down" or closed ("off") position shown in dotted line in FIG. 6. Movement of the lower convex portion 252 of the valve shell with respect to the fluid bore 212 controls the flow of fluid through the bore 212.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordance with the applicable patent laws and the rules promulgated under the authority thereof.

What is claimed is:

1. Valve apparatus for controlling the flow of intravenous fluids, comprising, in combination:

housing means, including a cylindrical portion having a bottom part;

inlet bore means connected to the bottom part of the housing means for providing a flow of fluid to the housing means;

outlet bore means connected to the bottom part of the housing means for providing a flow of fluid away from the housing means;

valve shell means disposed in the cylindrical portion of the housing means and having a portion movable in the housing means for controlling the flow of fluid through the housing means between the inlet bore means and the outlet bore means, including a radially outwardly extending flange adapted to be secured to the housing means, an outer cylindrical portion having a bottom portion secured to the flange and having a top portion, an inner cylinder portion movable upwardly and downwardly in the housing means for controlling the flow of fluid, a web connecting the inner cylinder portion to the top portion of the outer cylindrical portion, a bore in the inner cylinder portion, a pair of flanges spaced apart from each other in the bore and extending radially inwardly and defining an upper slot between them, a concave bottom closing the inner cylinder portion, a lower slot disposed between the concave bottom and the upper slot, and a convex bottom secured to the inner cylinder portion and movable therewith vertically upwardly and downwardly and comprising the exterior of the concave bottom;

valve core means disposed in the bore and secured to, and movable with, the valve shell means, including a first flange disposed in the upper slot of the valve shell means and a second flange disposed in the lower slot of the valve shell means for securing the valve core means and the valve shell means together, a convex bottom disposed in the concave bottom of the valve shell means, and a threaded bore; cap means including an outer cylinder wall having an upper portion and a lower portion, an inner cylinder wall spaced apart from the lower portion of the outer cylinder wall and disposed on the radially outwardly extending flange of the valve shell means for securing the valve shell means to the housing means, a circular bore defined between the lower portion of the outer cylinder wall and the inner cylinder wall for receiving the cylindrical portion of the housing means for securing the cap means to the housing means, a central wall secured to the outer cylinder wall between the upper and lower portions and to the inner cylinder wall, and an aperture extending through the central wall; and screw means rotatably secured to the valve core means for moving the valve core means and the valve shell means to control the flow of fluid through the housing means, including a head disposed on the central wall of the cap means and a threaded shank secured to the head and extending through the aperture in the central wall and into the threaded bore of the valve core.

2. The apparatus of claim 1 in which the housing means further includes a floor secured to the cylindrical portion, a valve seat extending through the floor, and a fluid bore disposed beneath the floor and communicating with the cylindrical portion through the valve seat.

3. The apparatus of claim 2 in which the first bore means and the second bore means are aligned with each other and connected to the fluid bore of the housing means.

4. The apparatus of claim 3 in which the valve shell means further includes a tip portion extending through the valve seat and into the fluid bore for controlling the flow of fluid through the fluid bore in response to movement of the valve shell means.

* * * * *